US009181297B1

(12) United States Patent
Pentelute et al.

(10) Patent No.: US 9,181,297 B1
(45) Date of Patent: Nov. 10, 2015

(54) CYSTEINE ARYLATION DIRECTED BY A GENETICALLY ENCODABLE π-CLAMP

(71) Applicants: Bradley L. Pentelute, Cambridge, MA (US); Chi Zhang, Cambridge, MA (US)

(72) Inventors: Bradley L. Pentelute, Cambridge, MA (US); Chi Zhang, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/278,060

(22) Filed: May 15, 2014

(51) Int. Cl.
    *A61K 38/00* (2006.01)
    *C07K 5/10* (2006.01)
    *C07K 7/04* (2006.01)
    *C07K 5/087* (2006.01)

(52) U.S. Cl.
    CPC ................................ *C07K 5/0812* (2013.01)

(58) Field of Classification Search
    CPC ..... A61K 38/00; A61K 47/4823; A61K 8/69; A61K 49/14; C07K 7/06; C07K 7/08
    See application file for complete search history.

(56) References Cited

U.S. PATENT DOCUMENTS

| 2007/0082378 A1 | 4/2007 | Kent et al. |
| 2011/0166392 A1 | 7/2011 | Umemoto |
| 2012/0004417 A1 | 1/2012 | Dimagno |
| 2014/0113871 A1 | 4/2014 | Pentelute et al. |

FOREIGN PATENT DOCUMENTS

WO    WO-2010/011313 A2    1/2010

OTHER PUBLICATIONS

Betts et al. "Amino Acid Properties and Consequences of Substitutions" in Bioinformatics for Geneticists, 2003, pp. 290-316.*
Chalker et al., "Methods for converting cysteine to dehydroalanine on peptides and proteins," Chem. Sci., 2(9):1666-1676 (2011).
Spokoyny et al., "A Perfluoroaryl-Cysteine $S_NAr$ Chemistry Approach to Unprotected Peptide Stapling," J. Am. Chem. Soc., 135(16):5946-5949 (2013).
Zhang et al., "Enzymatic "Click" Ligation: Selective Cysteine Modification in Polypeptides Enabled by Promiscuous Glutathione S-Transferase," Angew. Chem. Int. Ed., 52(52):14001-14005 (2013).
International Search Report and Written Opinion from PCT application PCT/US2013/062009 dated Mar. 18, 2014.

* cited by examiner

*Primary Examiner* — Marcela M Cordero Garcia
*Assistant Examiner* — Kaipeen Yang
(74) *Attorney, Agent, or Firm* — Foley Hoag LLP

(57) ABSTRACT

Disclosed are methods of single-site-specific cysteine modification on peptide/protein molecules under physiologically relevant conditions. This process features several significant advantages over existing methods of peptide modification, such as specificity towards thiols over other nucleophiles (e.g., amines, hydroxyls), excellent functional group tolerance, and mild reaction conditions. Especially important is the specificity observed for thiols appearing in an X-Cys-Pro-X sequence over other thiols or disulfides, where X is Phe, Trp, or Tyr; under the inventive conditions, other cysteines or reactive functional groups on the same peptide/protein chain are not functionalized.

17 Claims, 5 Drawing Sheets

CYSTEINE ARYLATION DIRECTED BY A GENETICALLY ENCODABLE π-CLAMP

GOVERNMENT SUPPORT

This invention was made with Government support under Grant No. GM110535 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Jul. 16, 2015, is named MTV-140.01(20021-14001)_SL.txt and is 3,402 bytes in size.

BACKGROUND

For many years researchers in the field of bioconjugate chemistry have needed well-defined ligation strategies that can be used for modification of biomolecules. Efficient bioconjugation strategies generally involve high levels of functional group tolerance, compatibility with water and other solvents, and efficient conversions (e.g., fast reaction times and high yields). Reactions that adhere to the principles of "click chemistry" are ideal candidates for bioconjugation applications. "Click" reactions are thermodynamically driven because the products have a highly favorable enthalpy of bonds. Several reactions can be classified as "click", including copper-catalyzed Huisgen's dipolar cycloadditions of azides and terminal alkynes, addition of thiols to alkenes, addition of isothiocyanates to amines, and Diels-Alder cycloadditions. Importantly, because the starting materials for these reactions are relatively stable, in principle they could be introduced to a wide range of macromolecules and hybrid materials. Furthermore, these reactions do not generate by-products and operate on reasonable timescales, making them attractive for use in bioconjugation.

Thiol modification is an important tool in the chemical, biological, medical, and material sciences. As the only thiol-containing amino acid, cysteine is typically used for protein modification using thiol-based reactions. Despite the ubiquity of cysteine tagging, general chemical approaches do not exist for the site-specific modification of a single cysteine in the presence of other unprotected cysteines within the same peptide/protein chain (FIG. 1A). Development of a general, robust, and highly efficient method that allows single-site-specific cysteine modification would significantly expand the ability to modify biomolecules.

SUMMARY

In certain embodiments, the invention relates to a method of making a compound according to Scheme 1:

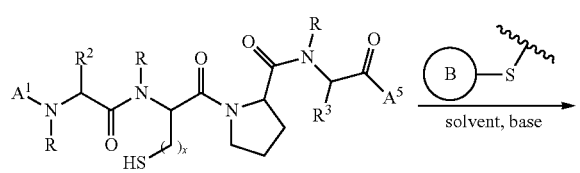

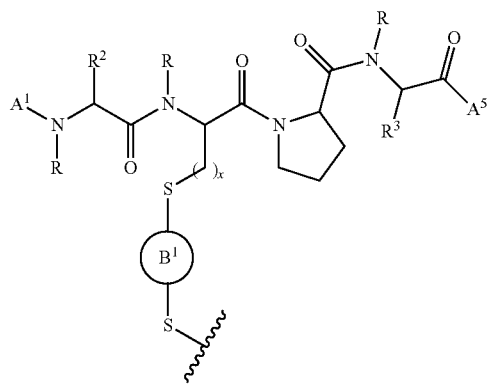

wherein, independently for each occurrence, base is a Bronsted base;

$A^1$ is H, an amine protecting group, a natural or unnatural alpha amino acid, a peptide, an oligopeptide, a polypeptide, or a protein;

$A^5$ is OH, a carboxylate protecting group, a natural or unnatural alpha amino acid, a peptide, an oligopeptide, a polypeptide, or a protein;

x is 0, 1, 2, 3, 4, 5, or 6;

R is H or alkyl;

$R^2$ is aralkyl or heteroaralkyl;

$R^3$ is aralkyl or heteroaralkyl; and

Ⓑ is a perfluorinated aryl radical.

In certain embodiments, the invention relates to any one of the methods described herein, wherein the base is triethylamine, $Na_3PO_4$, or tris(hydroxymethyl)aminomethane.

In certain embodiments, the invention relates to any one of the methods described herein, wherein $R^2$ is benzyl, indolylmethyl, or hydroxybenzyl.

In certain embodiments, the invention relates to any one of the methods described herein, wherein $R^3$ is benzyl, indolylmethyl, or hydroxybenzyl.

In certain embodiments, the invention relates to any one of the methods described herein, wherein R is H.

In certain embodiments, the invention relates to any one of the methods described herein, wherein x is 1, 2, or 3.

In certain embodiments, the invention relates to any one of the methods described herein, wherein Ⓑ is pentafluorophenyl or 4'-(2,2',3,3',4,5,5',6,6'-nonafluoro-1,1'-biphenyl).

In certain embodiments, the invention relates to any one of the methods described herein, wherein Ⓑ comprises at least one $^{18}F$ isotope.

In certain embodiments, the invention relates to a compound comprising substructure I or substructure II:

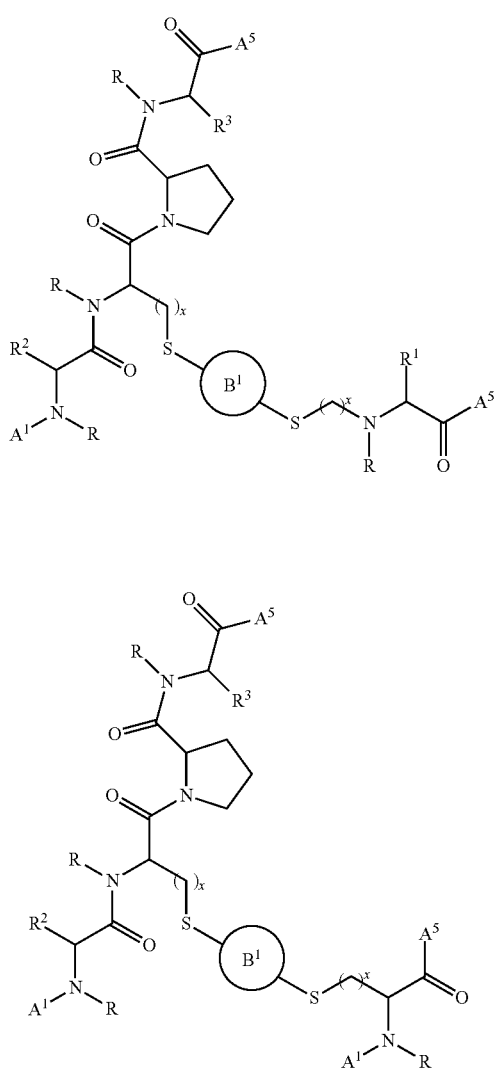

wherein, independently for each occurrence,

A¹ is H, an amine protecting group, a natural or unnatural alpha amino acid, a peptide, an oligopeptide, a polypeptide, or a protein;

A⁵ is OH, a carboxylate protecting group, a natural or unnatural alpha amino acid, a peptide, an oligopeptide, a polypeptide, or a protein;

Ⓑ is a perfluorinated aryl para-substituted diradical;

x is 0, 1, 2, 3, 4, 5, or 6;

R is H or alkyl;

R¹ is H, alkyl, thioalkyl, alkylthioalkyl, aralkyl, heteroaralkyl, hydroxyaralkyl, HO₂C-alkyl, H₂N—C(O)-alkyl, heterocycloalkyl, guanidinylalkyl, aminoalkyl, or hydroxyalkyl;

R² is aralkyl or heteroaralkyl; and

R³ is aralkyl or heteroaralkyl.

In certain embodiments, the invention relates to any one of the compounds described herein, wherein R² is benzyl, indolylmethyl, or hydroxybenzyl.

In certain embodiments, the invention relates to any one of the compounds described herein, wherein R³ is benzyl, or indolylmethyl, or hydroxybenzyl.

In certain embodiments, the invention relates to any one of the compounds described herein, wherein ¹ is 2,3,5,6-tetrafluorophenylene or 2,2',3,3',5,5',6,6'-octafluoro-1,1'-biphenyl-4,4'-ene.

In certain embodiments, the invention relates to any one of the compounds described herein, wherein R is H.

In certain embodiments, the invention relates to any one of the compounds described herein, wherein x is 1, 2, or 3.

In certain embodiments, the invention relates to any one of the compounds described herein, wherein the compound comprises a substructure selected from the group consisting of (peptides disclosed as SEQ ID NOS 1-2, respectively, in order of appearance):

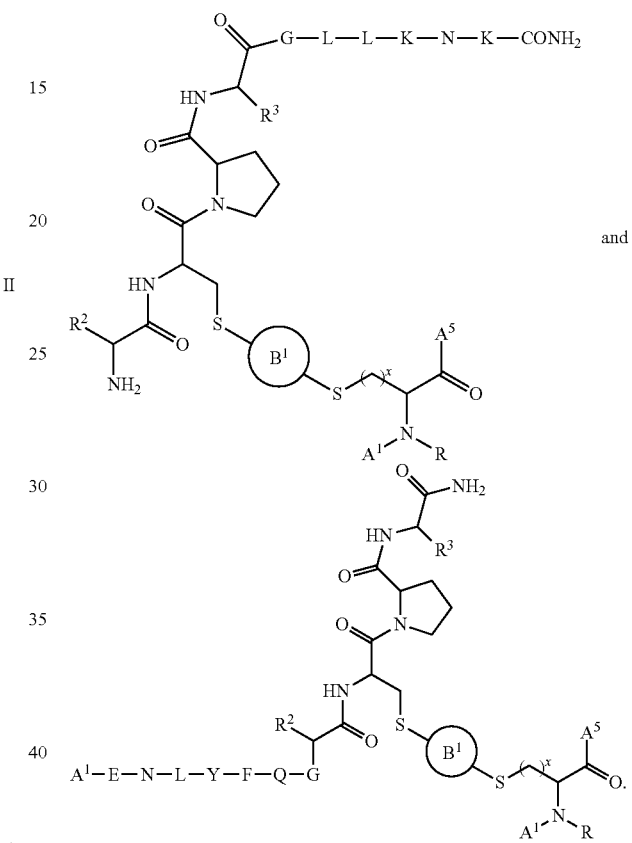

and

In certain embodiments, the invention relates to any one of the compounds described herein, wherein the compound comprises a substructure selected from the group consisting of (peptides disclosed as SEQ ID NOS 1-2, respectively, in order of appearance):

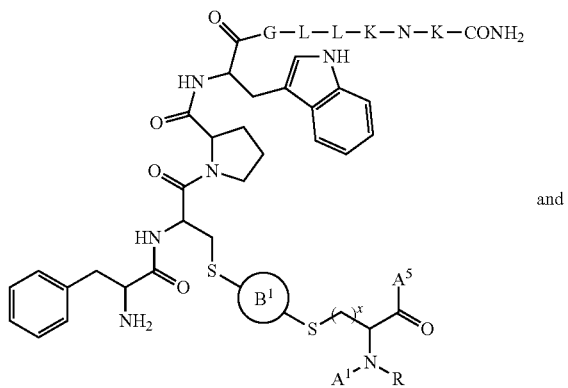

and

-continued

[Chemical structure showing A¹—E—N—L—Y—F—Q—G— linked peptide with cysteine-containing π-clamp structure, connected via sulfur to B¹ group, with another structure containing A⁵, A¹'—N—R]

In certain embodiments, the invention relates to any one of the compounds described herein, wherein [1] comprises at least one $^{18}$F isotope.

DETAILED DESCRIPTION

Overview

Figure 1:
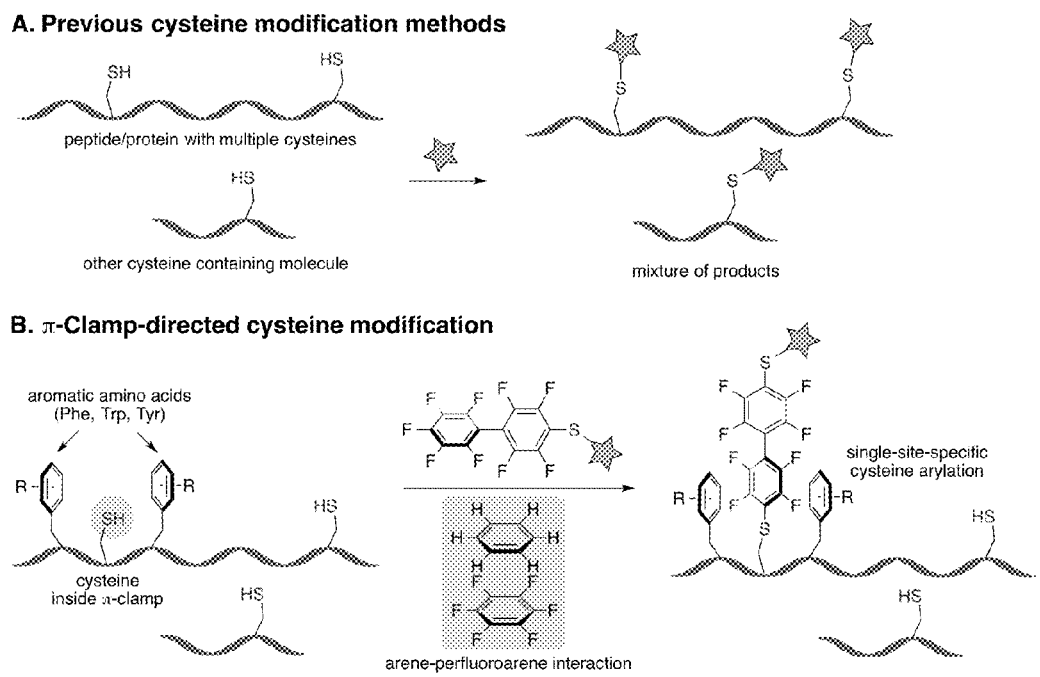
FIG. 1 depicts (A) that existing cysteine modification methods cannot selectively tag one unprotected cysteine in the presence of other unprotected cysteines. Use of these methods under these circumstances usually leads to product mixtures with heterogeneity in both regiochemistry and stoichiometry. (B) On the other hand, π-clamp directed cysteine modification is possible. The arene-perfluoroarene interaction between 4-mercaptoperfluoro-biphenyl moiety and aromatic amino acids side chains selectively directs the arylation of the cysteine within the π-clamp.

In certain embodiments, the invention relates to a method of single-site-specific modification of the side-chain thiol of a cysteine residue in a peptide/protein molecule under physiologically relevant conditions (FIG. 1B). This process has several significant advantages over existing methods of peptide modification, such as specificity for thiols over other nucleophiles (e.g., amines, hydroxyls), specificity towards specific thiols over other thiols or disulfides, excellent functional group tolerance, mild reaction conditions, and commercial availability of the relevant perfluorinated linkers and amino acids. The remarkable method requires only the presence of a relatively benign base, such as phosphate or TRIS, to deprotonate the thiol moiety. In certain embodiments, the invention relates to modification of the cysteine in a four-residue peptide subsequence, X-Cys-Pro-X, wherein X is an aromatic amino acid (e.g., Phe, Trp, or Tyr), while other cysteines or reactive functional groups on the same peptide/protein chain remain unchanged. The proline in this subsequence induces a β-turn formation, thus allowing the two aromatic amino acid residues to form a local "π-clamp" around the particular cysteine thiol. Unique arene-perfluoroarene interactions permit the recognition by the π-clamp of perfluoroaryl groups on biomolecules or chemical probes or reagents, which allows the site-specific arylation of the cysteine within the π-clamp.

In certain embodiments, the invention relates to site-specific arylation of a peptide comprising the substructure Phe-Cys-Pro-Phe (SEQ ID NO: 5). The arylation reaction is highly regioselective, thereby allowing modification of a single cysteine on various peptides and proteins, especially those with multiple disulfide bond and/or essential cysteine residues. The short Phe-Cys-Pro-Phe (SEQ ID NO: 5) subsequence may be engineered into the C-terminus, N-terminus, or flexible loops of a protein of interest by recombinant technologies. In certain embodiments, the method does not employ or require a catalyst or special conditions.

In certain embodiments, the invention is applicable to other molecules (i.e., in addition to peptides and proteins) comprising a plurality of thiols, wherein it is desirable selectively to modify a particular thiol.

Exemplary Methods

In certain embodiments, the invention relates to a method of making a compound according to Scheme 1:

Scheme 1

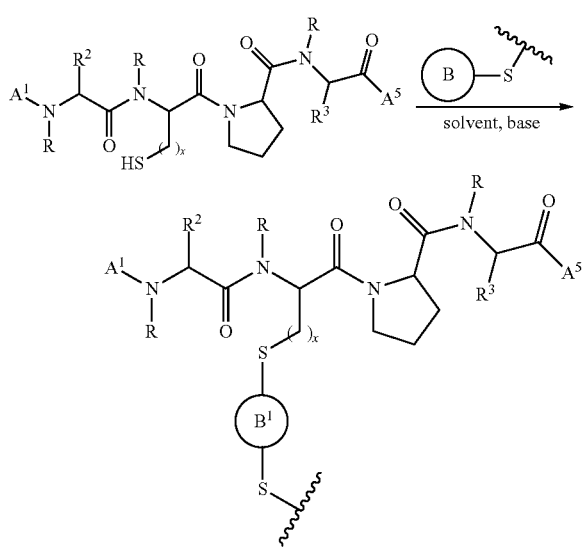

wherein, independently for each occurrence,
base is a Brønsted base;
$A^1$ is H, an amine protecting group, a natural or unnatural alpha amino acid, a peptide, an oligopeptide, a polypeptide, or a protein;
$A^5$ is OH, a carboxylate protecting group, a natural or unnatural alpha amino acid, a peptide, an oligopeptide, a polypeptide, or a protein;
x is 0, 1, 2, 3, 4, 5, or 6;
R is H or alkyl;
$R^2$ is aralkyl or heteroaralkyl;
$R^3$ is aralkyl or heteroaralkyl; and
Ⓑ is a perfluorinated aryl radical.

In certain embodiments, the invention relates to any one of the aforementioned methods, wherein the compound is a compound comprising substructure I or substructure II.

In certain embodiments, the invention relates to any one of the aforementioned methods, wherein the solvent is water, DMF, $CH_3CN$, $CH_3OH$, $CH_3CH_2OH$, isopropanol, DMSO, dibutyl ether, tetrahydrofuran (THF), 1,4-dioxane, DME, dichloromethane, dichloroethane, acetone, diethyl ether, hexanes, or a mixture thereof.

In certain embodiments, the invention relates to any one of the aforementioned methods, wherein the base is triethylamine, $Na_3PO_4$, or tris(hydroxymethyl)aminomethane (TRIS), ethyl acetate, $Na_2CO_3$, imidazole, 3-morpholinopropane-1-sulfonic acid (MOPS), 2-[4-(2-hydroxyethyl)piperazin-1-yl]ethanesulfonic acid (HEPES), 3-[[1,3-dihydroxy-2-(hydroxymethyl)propan-2-yl]amino]propane-1-sulfonic acid (TAPS), 3-(cyclohexylamino)-1-propanesulfonic acid (CAPS), 2-[[1,3-dihydroxy-2-(hydroxymethyl)propan-2-yl]amino]ethanesulfonic acid (TES).

In certain embodiments, the invention relates to any one of the aforementioned methods, wherein $R^2$ is benzyl. In certain embodiments, the invention relates to any one of the aforementioned methods, wherein $R^2$ is indolylmethyl. In certain embodiments, the invention relates to any one of the aforementioned methods, wherein $R^2$ is 3-indolylmethyl. In certain embodiments, the invention relates to any one of the aforementioned methods, wherein $R^2$ is hydroxybenzyl. In certain embodiments, the invention relates to any one of the aforementioned methods, wherein $R^2$ is 4-hydroxybenzyl.

In certain embodiments, the invention relates to any one of the aforementioned methods, wherein $R^3$ is benzyl. In certain embodiments, the invention relates to any one of the aforementioned methods, wherein $R^3$ is indolylmethyl. In certain embodiments, the invention relates to any one of the aforementioned methods, wherein $R^3$ is 3-indolylmethyl. In certain embodiments, the invention relates to any one of the aforementioned methods, wherein $R^3$ is hydroxybenzyl. In certain embodiments, the invention relates to any one of the aforementioned methods, wherein $R^3$ is 4-hydroxybenzyl.

In certain embodiments, the invention relates to any one of the aforementioned methods, wherein $A^1$ is an amine protecting group selected from the group consisting of an N,O-acetal, allyloxycarbonyl (Aloc), benzyl (Bn), benzyloxycarbonyl (Cbz), benzyloxymethyl (BOM), t-butoxycarbonyl (Boc), t-butyldimethylsilyl (TBDMS), t-butyldiphenylsilyl (TBDPS), diphenylmethyl, diphenylmethylene, ethoxycarbonyl, 9-fluorenylmethoxycarbonyl (Fmoc), p-methoxybenzyl (PMB), methoxycarbonyl, methoxymethyl (MOM), p-methoxyphenyl (PMP), p-nitrocinnamyloxycarbonyl (Noc), tosyl (Ts), 2-tosylethoxycarbonyl (Tsoc), 2,2,2-trichloroethoxycarbonyl (Troc), trifluoroacetyl, triisopropylsilyl (TIPS), trimethylsilyl (TMS), 2-(trimethylsilyl)ethoxycarbonyl (Teoc), 2-(trimethylsilyl)ethoxymethyl (SEM), or trityl (Tr).

In certain embodiments, the invention relates to any one of the aforementioned methods, wherein $A^5$ is a carboxylate protecting group selected from the group consisting of allyl, benzyl, benzyloxymethyl (BOM), t-Bu, t-butyldimethylsilyl (TBDMS), t-butyldiphenylsilyl (TBDPS), diphenylmethyl, 9-fluorenylmethyl (Fm), 2-methoxyethoxymethyl (MEM), methoxymethyl (MOM), p-nitrobenzyl (PNB), an ester, a 1,3-oxazoline, pivaloyloxymethyl (Pom), 2-tosylethyl (TSE), 2,2,2-trichloroethyl (TCE), triethylsilyl (TES), trimethylsilyl (TMS), 2-(trimethylsilyl)ethoxymethyl (SEM), or 2-(trimethylsilyl)ethyl (TMSE).

In certain embodiments, the invention relates to any one of the aforementioned methods, wherein R is H.

In certain embodiments, the invention relates to any one of the aforementioned methods, wherein x is 1, 2, or 3. In certain embodiments, the invention relates to any one of the aforementioned methods, wherein x is 1.

In certain embodiments, the invention relates to any one of the aforementioned methods, wherein Ⓑ is pentafluorophenyl or 4'-(2,2',3,3',4,5,5',6,6'-nonafluoro-1,1'-biphenyl).

In certain embodiments, the invention relates to any one of the aforementioned methods, wherein the temperature is between about 10° C. and about 50° C. In certain embodiments, the invention relates to any one of the aforementioned methods, wherein the temperature is about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., or about 40° C.

The reactions typically proceed at mild temperatures and pressures to give high yields of the product. Thus, yields of desired products greater than 45%, greater than 75%, greater than 80%, greater than 85%, greater than 90%, or greater than 95% may be obtained from reactions at mild temperatures according to the invention.

In certain embodiments, the reactions take place under an inert atmosphere of a gas such as nitrogen or argon.

The reaction processes of the invention can be conducted in continuous, semi-continuous or batch fashion and may involve a liquid recycle operation as desired. The processes of this invention are preferably conducted in batch fashion. Likewise, the manner or order of addition of the reaction ingredients, base, and solvent are not generally critical to the success of the reaction, and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. When complete conversion is not desired or not obtainable, the starting materials can be separated from the product and then recycled back into the reaction zone.

The processes may be conducted in glass lined, stainless steel, fluoropolymer coated (e.g., Teflon coated) or similar type reaction equipment. The reaction zone may be fitted with one or more internal and/or external heat exchanger(s) in order to control undue temperature fluctuations, or to prevent any possible "runaway" reaction temperatures.

Furthermore, one or more of the reactants can be immobilized on or incorporated into a polymer or other insoluble matrix by, for example, derivatization with one or more of the substituents of the aryl group or an amino acid residue.

The ability to provide synthesis schemes for the compounds of the invention that can be carried out under mild conditions has broad application.

In addition, the subject methods can be used as part of combinatorial synthesis schemes to yield libraries of compounds. Accordingly, another aspect of the invention relates to use of the subject method to generate variegated libraries of compounds, and to the libraries themselves. The libraries can be soluble or linked to insoluble supports, e.g., through a substituent of a reactant (prior to carrying out a reaction of the invention).

Further, the methods of the invention can be used to produce synthetic intermediates that, after being subjected to additional methods known in the art, are transformed to desired end products.

Exemplary Compounds

In certain embodiments, the invention relates to a compound comprising substructure I:

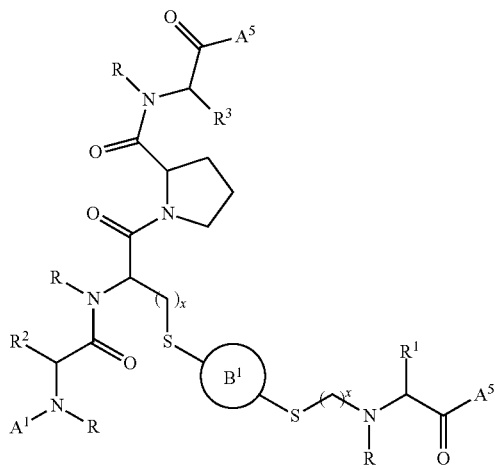

wherein, independently for each occurrence, $A^1$ is H, an amine protecting group, a natural or unnatural alpha amino acid, a peptide, an oligopeptide, a polypeptide, or a protein;

$A^5$ is OH, a carboxylate protecting group, a natural or unnatural alpha amino acid, a peptide, an oligopeptide, a polypeptide, or a protein;

$B^1$ is a perfluorinated aryl para-substituted diradical;

x is 0, 1, 2, 3, 4, 5, or 6;

R is H or alkyl;

$R^1$ is H, alkyl, thioalkyl, alkylthioalkyl, aralkyl, heteroaralkyl, hydroxyaralkyl, $HO_2C$-alkyl, $H_2N$—C(O)-alkyl, heterocycloalkyl, guanidinylalkyl, aminoalkyl, or hydroxyalkyl;

$R^2$ is aralkyl or heteroaralkyl; and $R^3$ is aralkyl or heteroaralkyl.

In certain embodiments, the invention relates to a compound comprising substructure II:

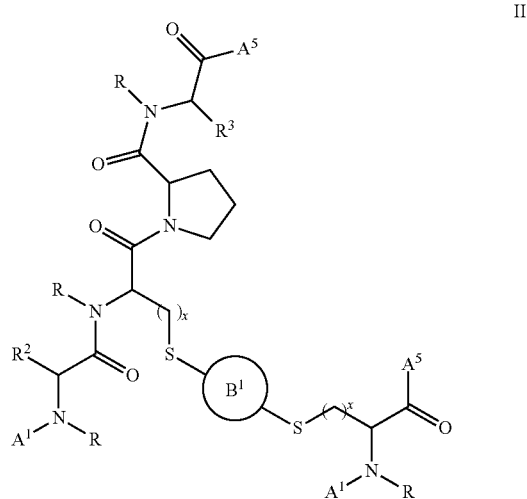

wherein, independently for each occurrence, $A^1$ is H, an amine protecting group, a natural or unnatural alpha amino acid, a peptide, an oligopeptide, a polypeptide, or a protein;

$A^5$ is OH, a carboxylate protecting group, a natural or unnatural alpha amino acid, a peptide, an oligopeptide, a polypeptide, or a protein;

x is 0, 1, 2, 3, 4, 5, or 6;

$B^1$ is a perfluorinated aryl para-substituted diradical;

R is H or alkyl;

$R^2$ is aralkyl or heteroaralkyl; and $R^3$ is aralkyl or heteroaralkyl.

In certain embodiments, the invention relates to any one of the aforementioned compounds, wherein $R^2$ is benzyl. In certain embodiments, the invention relates to any one of the aforementioned compounds, wherein $R^2$ is indolylmethyl. In certain embodiments, the invention relates to any one of the aforementioned compounds, wherein $R^2$ is 3-indolylmethyl. In certain embodiments, the invention relates to any one of the aforementioned compounds, wherein $R^2$ is hydroxybenzyl. In certain embodiments, the invention relates to any one of the aforementioned compounds, wherein $R^2$ is 4-hydroxybenzyl.

In certain embodiments, the invention relates to any one of the aforementioned compounds, wherein $R^3$ is benzyl. In certain embodiments, the invention relates to any one of the aforementioned compounds, wherein $R^3$ is indolylmethyl. In certain embodiments, the invention relates to any one of the aforementioned compounds, wherein $R^3$ is 3-indolylmethyl. In certain embodiments, the invention relates to any one of the aforementioned compounds, wherein $R^3$ is hydroxybenzyl. In certain embodiments, the invention relates to any one of the aforementioned compounds, wherein $R^3$ is 4-hydroxybenzyl.

In certain embodiments, the invention relates to any one of the aforementioned compounds, wherein $A^1$ is an amine protecting group selected from the group consisting of an N,O-acetal, allyloxycarbonyl (Aloc), benzyl (Bn), benzyloxycarbonyl (Cbz), benzyloxymethyl (BOM), t-butoxycarbonyl (Boc), t-butyldimethylsilyl (TBDMS), t-butyldiphenylsilyl (TBDPS), diphenylmethyl, diphenylmethylene, ethoxycarbonyl, 9-fluorenylmethoxycarbonyl (Fmoc), p-methoxybenzyl (PMB), methoxycarbonyl, methoxymethyl (MOM), p-methoxyphenyl (PMP), p-nitrocinnamyloxycarbonyl (Noc), tosyl (Ts), 2-tosylethoxycarbonyl (Tsoc), 2,2,2-trichloroethoxycarbonyl (Troc), trifluoroacetyl, triisopropylsilyl (TIPS), trimethylsilyl (TMS), 2-(trimethylsilyl)ethoxycarbonyl (Teoc), 2-(trimethylsilyl)ethoxymethyl (SEM), or trityl (Tr).

In certain embodiments, the invention relates to any one of the aforementioned compounds, wherein $A^5$ is a carboxylate protecting group selected from the group consisting of allyl, benzyl, benzyloxymethyl (BOM), t-Bu, t-butyldimethylsilyl (TBDMS), t-butyldiphenylsilyl (TBDPS), diphenylmethyl, 9-fluorenylmethyl (Fm), 2-methoxyethoxymethyl (MEM), methoxymethyl (MOM), p-nitrobenzyl (PNB), an ester, a 1,3-oxazoline, pivaloyloxymethyl (Pom), 2-tosylethyl (TSE), 2,2,2-trichloroethyl (TCE), triethylsilyl (TES), trimethylsilyl (TMS), 2-(trimethylsilyl)ethoxymethyl (SEM), or 2-(trimethylsilyl)ethyl (TMSE).

In certain embodiments, the invention relates to any one of the aforementioned compounds, wherein $^1$ is 2,3,5,6-tetrafluorophenylene or 2,2',3,3',5,5',6,6'-octafluoro-1,1'-biphenyl-4,4'-ene.

In certain embodiments, the invention relates to any one of the aforementioned compounds, wherein R is H.

In certain embodiments, the invention relates to any one of the aforementioned compounds, wherein x is 1, 2, or 3. In certain embodiments, the invention relates to any one of the aforementioned compounds, wherein x is 1.

In certain embodiments, the invention relates to any one of the aforementioned compounds, wherein $R^1$, where present, is aminoalkyl or aralkyl. In certain embodiments, the invention relates to any one of the aforementioned compounds, wherein R', where present, is —(CH$_2$)$_4$—NH$_2$. In certain embodiments, the invention relates to any one of the aforementioned compounds, wherein $R^1$, where present, is benzyl.

In certain embodiments, the invention relates to any one of the aforementioned compounds, wherein the compound comprises the following substructure (peptide disclosed as SEQ ID NO: 1):

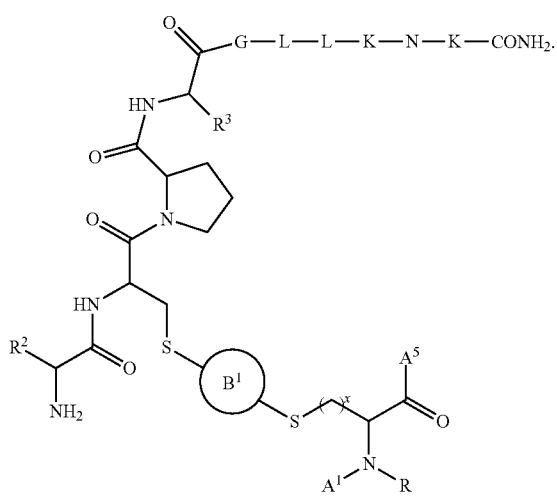

In certain embodiments, the invention relates to any one of the aforementioned compounds, wherein the compound comprises the following substructure (peptide disclosed as SEQ ID NO: 1):

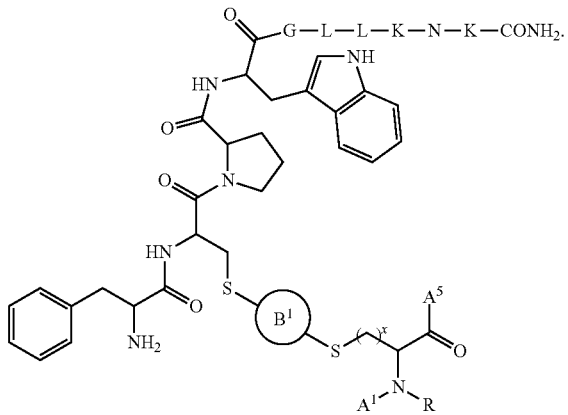

In certain embodiments, the invention relates to any one of the aforementioned compounds, wherein the compound comprises the following substructure (peptide disclosed as SEQ ID NO: 2):

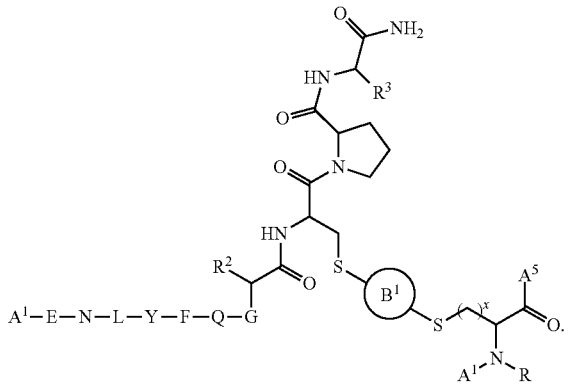

In certain embodiments, the invention relates to any one of the aforementioned compounds, wherein the compound comprises the following substructure (peptide disclosed as SEQ ID NO: 2):

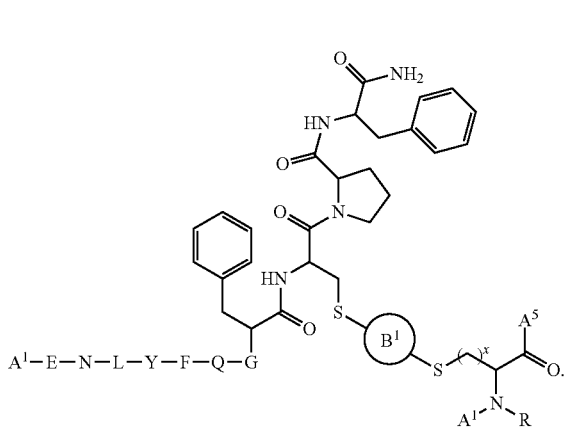

In certain embodiments, the invention relates to any one of the aforementioned compounds, wherein at least one C—F bond has been replaced with a C-Nu bond; and —Nu is —CN, —I, —N$_3$, —OR, —CCR, or —NR$_2$.

In certain embodiments, the invention relates to any one of the aforementioned compounds, wherein at least one fluorine atom has been replaced with $^{18}$F isotope.

In certain embodiments, the invention relates to any one of the compounds described herein.

Exemplary Conjugated Compounds

In certain embodiments, the invention relates to a hybrid composition, wherein the hybrid composition comprises a linker, any one of the aforementioned compounds, and a detectable moiety; and the linker links the compound to the detectable moiety.

In certain embodiments, the invention relates to any one of the aforementioned hybrid compositions, wherein the detectable moiety is a fluorescent moiety, a dye moiety, a radionuclide, a drug molecule, an epitope, or an MRI contrast agent.

In certain embodiments, the invention relates to a hybrid composition, wherein the hybrid composition comprises a linker, any one of the aforementioned compounds, and a biomolecule; and the linker links the compound to the biomolecule.

In certain embodiments, the invention relates to any one of the aforementioned hybrid compositions, wherein the biomolecule is a protein.

In certain embodiments, the invention relates to any one of the aforementioned hybrid compositions, wherein the protein is an antibody.

In certain embodiments, the invention relates to any one of the aforementioned hybrid compositions, wherein the biomolecule is DNA, RNA, or peptide nucleic acid (PNA).

In certain embodiments, the invention relates to any one of the aforementioned hybrid compositions, wherein the biomolecule is siRNA.

In certain embodiments, the invention relates to a hybrid composition, wherein the hybrid composition comprises a linker, any one of the aforementioned compounds, and a polymer; and the linker links the compound to the polymer.

In certain embodiments, the invention relates to any one of the aforementioned hybrid compositions, wherein the polymer is polyethylene glycol.

In certain embodiments, the invention relates to any one of the hybrid compositions described herein.

Exemplary Peptides, Oligopeptides, Polypeptides, and Proteins

In certain embodiments, the invention relates to a peptide, an oligopeptide, a polypeptide, or a protein, wherein the peptide, oligopeptide, polypeptide, or protein comprises substructure I or substructure II.

In certain embodiments, the invention relates to a peptide, an oligopeptide, a polypeptide, or a protein, wherein the peptide, oligopeptide, polypeptide, or protein comprises a plurality of substructures selected from the group consisting of substructure I and substructure II.

In certain embodiments, the invention relates to any one of the peptides, oligopeptides, polypeptides, or proteins described herein.

Exemplary Therapeutic Methods

Antibody-drug conjugates (ADCs) are an emerging class of anti-cancer therapeutics. Highly cytotoxic small molecule drugs are conjugated to antibodies to create a single molecular entity. ADCs combine the high efficacy of small molecules with the target specificity of antibodies to enable the selective delivery of drug payloads to cancerous tissues, which reduces the systematic toxicity of conventional small molecule drugs.

Traditionally, ADCs are prepared by conjugating small molecule drugs to either cysteines generated from reducing an internal disulfide bond or surface-exposed lysines. Because multiple lysines and cysteines are present in antibodies, these conventional approaches usually lead to heterogeneous products with undefined drug-antibody ratio, which might cause difficulty for manufacturing and characterization. Furthermore, each individual antibody-drug conjugate may exhibit different pharmacokinetics, efficacy, and safety profiles, hindering a rational approach to optimizing ADC-based cancer treatment.

Recent studies showed that ADCs prepared using site-specific conjugation techniques exhibited improved pharmacological profiles.

So, in certain embodiments, the invention relates to an ADC with defined position of drug-attachment and defined drug to antibody ratio. In certain embodiments, the ADCs of the invention permit rational optimization of ADC-based therapies. In certain embodiments, the ADC comprises a structure of any one of the compounds described herein.

In certain embodiments, the invention relates to any one of the ADCs mentioned herein, comprising monomethyl auristatin E (MMAE) covalently conjugated to an antibody, wherein the antibody targets a cell surface receptor that is over-expressed in a cancer cell. MMAE is a highly toxic antimitotic agent that inhibits cell division by blocking tubulin polymerization. MMAE has been successfully conjugated to antibodies targeting human CD30 to create ADCs that have been approved by FDA to treat Hodgkin lymphoma as well as anaplastic large-cell lymphoma.

In certain embodiments, the invention relates to any one of the ADCs mentioned herein, wherein the antibody targets cell receptors CD30, CD22, CD33, human epidermal growth factor receptor 2 (HER2), or epidermal growth factor receptor (EGFR). It should be noted that by conjugating drugs to antibodies targeting different receptors, the ADCs prepared should be useful for treating different cancers.

Definitions

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

The term "heteroatom" is art-recognized and refers to an atom of any element other than carbon or hydrogen. Illustrative heteroatoms include boron, nitrogen, oxygen, phosphorus, sulfur and selenium.

The term "alkoxy" means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxycarbonyl" means an alkoxy group, as defined herein, appended to the parent molecular moiety through a carbonyl group, represented by —C(=O)—, as defined herein. Representative examples of alkoxycarbonyl include, but are not limited to, methoxycarbonyl, ethoxycarbonyl, and tert-butoxycarbonyl.

The term "alkyl" means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy" and "arylcarbonyloxy" as used herein, means an alkylcarbonyl or arylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. Representative examples of arylcarbonyloxy include, but are not limited to phenylcarbonyloxy.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio. The terms "arylthio," "alkenylthio" and "arylakylthio," for example, are likewise defined.

The term "amido" as used herein, means —NHC(=O)—, wherein the amido group is bound to the parent molecular moiety through the nitrogen. Examples of amido include alkylamido such as $CH_3C(=O)N(H)$— and $CH_3CH_2C(=O)N(H)$—.

The term "amino" as used herein, refers to radicals of both unsubstituted and substituted amines appended to the parent molecular moiety through a nitrogen atom. The two groups are each independently hydrogen, alkyl, alkylcarbonyl, alkylsulfonyl, arylcarbonyl, or formyl. Representative examples include, but are not limited to methylamino, acetylamino, and acetylmethylamino.

The term "aromatic" refers to a planar or polycyclic structure characterized by a cyclically conjugated molecular moiety containing 4n+2 electrons, wherein n is the absolute value of an integer. Aromatic molecules containing fused, or joined, rings also are referred to as bicyclic aromatic rings. For example, bicyclic aromatic rings containing heteroatoms in a hydrocarbon ring structure are referred to as bicyclic heteroaryl rings.

The term "aryl," as used herein, means a phenyl group or a naphthyl group. The aryl groups of the invention can be optionally substituted with 1, 2, 3, 4 or 5 substituents independently selected from the group consisting of alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, phosphinyl, silyl and silyloxy.

The term "arylene," is art-recognized, and as used herein, pertains to a bidentate moiety obtained by removing two hydrogen atoms of an aryl ring, as defined above.

The term "arylalkyl" or "aralkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "carbonyl" as used herein, means a —C(=O)— group.

The term "carboxy" as used herein, means a —$CO_2H$ group.

The term "cyano" as used herein, means a —CN group.

The term "halo" or "halogen" means —Cl, —Br, —I or —F.

The term "haloalkyl" means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heterocyclyl", as used herein, include non-aromatic, ring systems, including, but not limited to, monocyclic, bicyclic and tricyclic rings, which can be completely saturated or which can contain one or more units of unsaturation, for the avoidance of doubt, the degree of unsaturation does not result in an aromatic ring system) and have 3 to 12 atoms including at least one heteroatom, such as nitrogen, oxygen, or sulfur. For purposes of exemplification, which should not be construed as limiting the scope of this invention, the following are examples of heterocyclic rings: azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl. The heterocyclyl groups of the invention are substituted with 0, 1, 2, 3, 4 or 5 substituents independently selected from alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, phosphinyl, silyl and silyloxy.

The term "heteroaryl" as used herein, include aromatic ring systems, including, but not limited to, monocyclic, bicyclic and tricyclic rings, and have 3 to 12 atoms including at least one heteroatom, such as nitrogen, oxygen, or sulfur. For purposes of exemplification, which should not be construed as limiting the scope of this invention: azaindolyl, benzo(b) thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups of the invention are substituted with 0, 1, 2, 3, 4 or 5 substituents independently selected from alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, phosphinyl, silyl and silyloxy.

The term "heteroarylene," is art-recognized, and as used herein, pertains to a bidentate moiety obtained by removing two hydrogen atoms of a heteroaryl ring, as defined above.

The term "heteroarylalkyl" or "heteroaralkyl" as used herein, means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl) ethyl.

The term "hydroxy" as used herein, means an —OH group.

The term "hydroxyalkyl" as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein, means a —SH group.

The term "nitro" as used herein, means a —$NO_2$ group.

The term "silyl" as used herein includes hydrocarbyl derivatives of the silyl ($H_3Si$—) group (i.e., (hydrocarbyl)$_3Si$—), wherein a hydrocarbyl groups are univalent groups formed by removing a hydrogen atom from a hydrocarbon, e.g., ethyl, phenyl. The hydrocarbyl groups can be combinations of differing groups which can be varied in order to provide a number of silyl groups, such as trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy" as used herein means a silyl group, as defined herein, is appended to the parent molecule through an oxygen atom.

The definition of each expression, e.g., alkyl, m, n, and the like, when it occurs more than once in any structure, is intended to be independent of its definition elsewhere in the same structure.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations.

Certain compounds contained in compositions of the invention may exist in particular geometric or stereoisomeric forms. In addition, polymers of the invention may also be optically active. The invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991). Protected forms of the inventive compounds are included within the scope of this invention.

For purposes of this invention, the chemical elements are identified in accordance with the Periodic Table of the Elements, CAS version, Handbook of Chemistry and Physics, 67th Ed., 1986-87, inside cover.

EXEMPLIFICATION

The invention now being generally described, it will be more readily understood by reference to the following examples, which are included merely for purposes of illustration of certain aspects and embodiments of the invention, and are not intended to limit the invention.

Example 1

Model Peptides

An enzymatic "click" ligation for site-specific cysteine modification based on perfluoroaryl-cysteine $S_NAr$ "click" reaction and glutathione S-transferase (GST) catalysis is described in International Patent Application publication number WO 14/052650, which is hereby incorporated by reference in its entirety.

Figure 2:
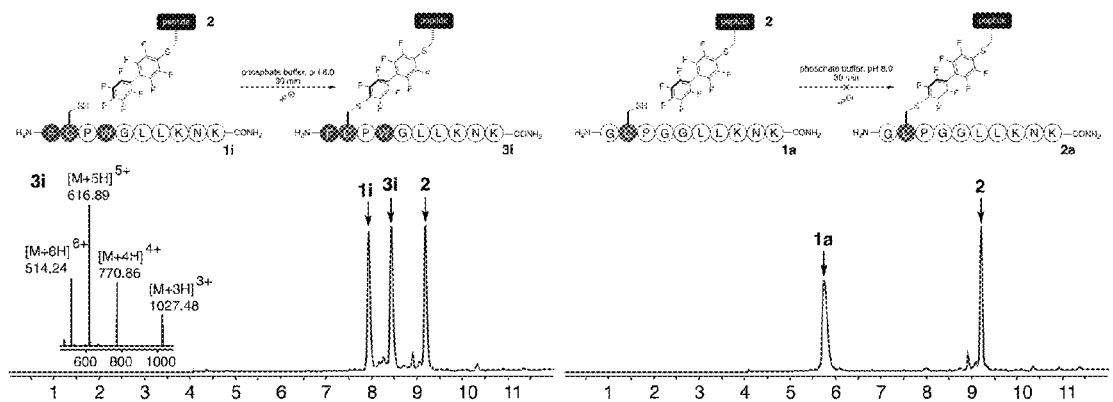
FIG. 2 depicts the ligation of two peptides by π-clamp-directed cysteine arylation (peptides disclosed as SEQ ID NOS 7, 7, 8 and 8, respectively, in order of appearance). Reaction conditions: 1 mM peptide 1i or 1a, 1 mM peptide 2, 0.2 M phosphate, 20 mM TCEP.HCl, pH 8.0, 37° C., 30 min. Sequence of peptide 2: Biotin-ENLYFQGC*KKK-CONH$_2$ (SEQ ID NO: 3), C* represents the modified cysteine. Chromatograms shown were total ion currents (TIC) from LC-MS analysis of the crude reaction mixtures. Mass spectrum shown was taken from the highest point of the TIC peak. TCEP: tris(2-carboxyethyl)phosphine. Amino acids are shown in single-letter codes.

A four-residue peptide sequence, Phe-Cys-Pro-Trp (SEQ ID NO: 6), was discovered that exhibited unusually high reactivity with perfluoroaryl-modified peptide electrophiles. Two model peptides were synthesized, one containing the Phe-Cys-Pro-Trp (SEQ ID NO: 6), and another one with both phenylalanine and tryptophan mutated to glycine. Reacting 1 mM peptide 1i with 1 mM peptide 2 in phosphate buffer, pH 8.0 at 37° C. for 30 minutes yielded 36% of the arylated product 3i as confirmed by LC-MS analysis of the crude reaction mixture (FIG. 2, left chromatogram). Mutating both the phenylalanine and tryptophan to glycine completely eliminated the reactivity and showed no product formation at same reaction conditions (FIG. 2, right chromatogram), which was consistent with previous findings that the $S_NAr$ reaction between cysteine and perfluoroaryl group is sluggish in aqueous media. It is well-documented that arene-perfluoroarene interactions are involved in various chemical and biological recognition processes. While not wishing to be bound by any particular theory, this apparently increased $S_NAr$ reaction rate for the Phe-Cys-Pro-Trp sequence (SEQ ID NO: 6) might be the result of π-interactions between the Phe/Trp and the perfluoroarene group. In addition, the existence of a proline may aid this process by promoting the formation of a β-turn that organizes the Phe and Trp to a more structured π-clamp around the cysteine, which may help to enhance the $S_NAr$ reaction rate of the cysteine inside the π-clamp with the perfluoroaryl group.

Example 2

X-Cys-Pro-X

Figure 3:
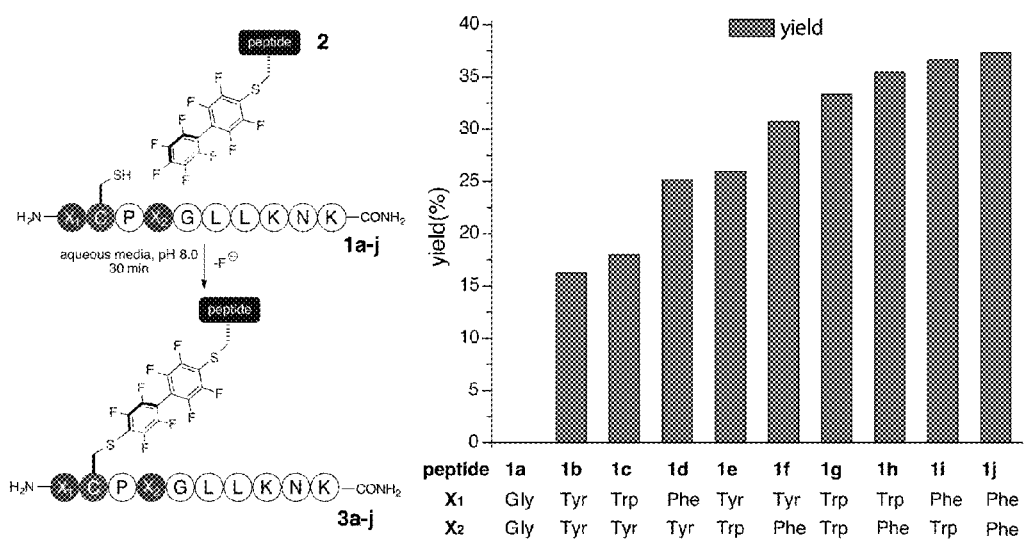
FIG. 3 depicts the results of screening combinations of aromatic amino acids for their ability to confer π-clamp directed cysteine arylation (peptides disclosed as SEQ ID NOS 9 and 9, respectively, in order of appearance). Reaction conditions: 1 mM peptide 1a-j, 1 mM peptide 2, 0.2 M phosphate, 20 mM TCEP.HCl, pH 8.0, 37° C., 30 min. Reaction yields were calculated from UV absorption at 214 nm obtained from HPLC analysis of the crude reaction mixture.

All combinations of genetically encodable amino acids were screened for the formation of the π-clamp. In addition to peptide 1a and 1i, 8 peptides were prepared to cover all possible aromatic amino acids combinations at X positions of X-Cys-Pro-X sequence. LC-MS and HPLC analysis of crude reactions revealed that all aromatic amino acids-containing peptides 1b-j were selectively arylated by the perfluoroaryl-modified peptide 2, while no product was observed with the double glycine mutant 1a (FIG. 3). Peptide with phenylalanine or tryptophan (peptides 1g-j) showed superior reactivity compared to peptide containing tyrosine (peptides 1b-f), and peptide 1j with two phenylalanines showed the highest reactivity leading to more than 37% product formation within 30 minutes.

Example 3

Chemo- and Reioselectivity of the Arylation Reaction

Figure 4:
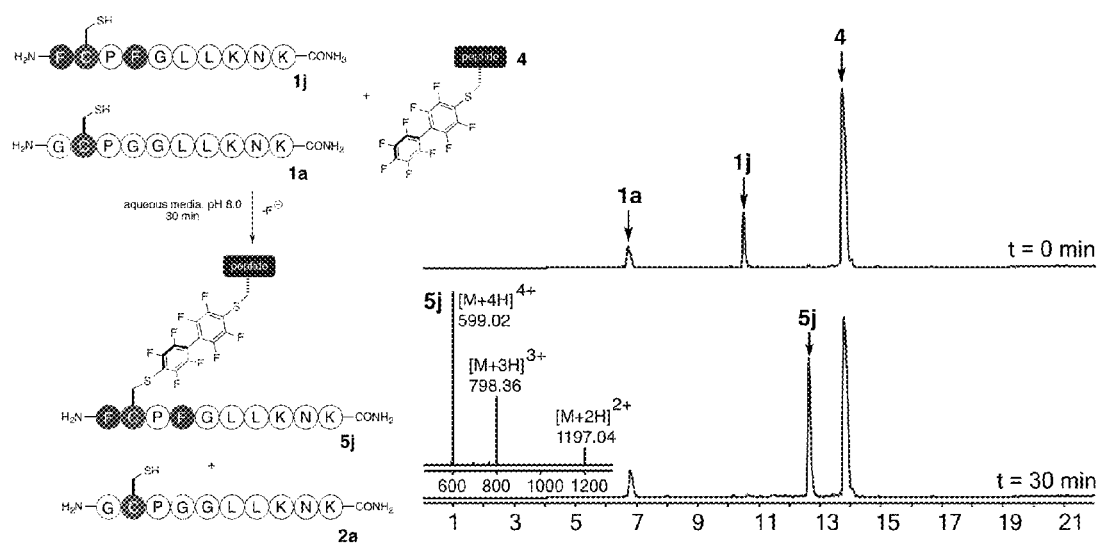
FIG. 4 depicts the selective arylation of cysteine inside the Phe-Phe π-clamp in the presence of a competing cysteine-containing peptide (peptides disclosed as SEQ ID NOS 10, 8, 10 and 8, respectively, in order of appearance). Reaction conditions: 1 mM peptide 2j, 1 mM peptide 2a, 5 mM peptide 4, 0.2 M phosphate, 20 mM TCEP.HCl, 37° C. Only the cysteine inside the π-clamp was arylated; no arylated product was observed for competing peptide 2a. LC-MS traces shown are total ion currents (TIC). The mass spectrum shown was acquired at the highest point of the TIC peak. Sequence of peptide 4: NH$_2$—VTLPSTC*GAS-CONH$_2$ (SEQ ID NO: 4), wherein C* represents the modified cysteine.
Figure 5:
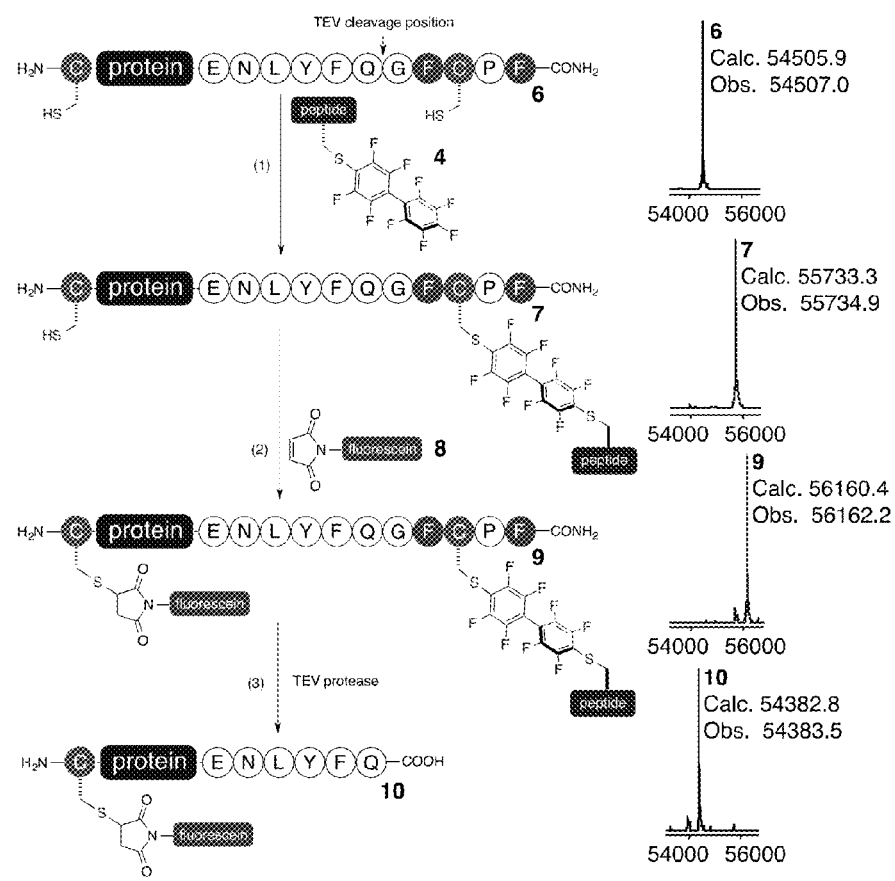
FIG. 5 depicts sequential labeling of two unprotected cysteines (one within a π-clamp; another at the N-terminus) in a 55 kDa protein molecule. The model protein used was a fused protein of anthrax toxin lethal factor 1-263 (LF$_N$) and diphtheria toxin domain A (DTA) (peptides disclosed as SEQ ID NOS 11, 11, 11 and 12, respectively, in order of appearance). Reaction conditions: (1) 50 μM protein 6, 1 mM peptide 4, 0.2 M phosphate, 20 mM TCEP.HCl, 37° C., 2 hours. Only the cysteine inside the π-clamp was arylated; no reaction was observed on the N-terminal cysteine. (2) 50 μM protein 7, 1 mM fluorescein-5-maleimide 8, 0.2 M phosphate, room temperature, 10 minutes. (3) 25 μM protein 9, 0.1 mg/mL TEV protease, 50 mM Tris.HCl, 0.1 mM EDTA, 1 mM DTT, pH 8.0, room temperature, 15 hours. All masses shown were deconvoluted masses of whole protein TIC peaks from LC-MS analysis of the crude reaction mixtures. TEV: tobacco itch virus; EDTA: ethylenediaminetetraacetic acid; DTT: dithiothreitol; Tris: 2-amino-2-hydroxylmethyl-propane-1,3-diol.

The chemo- and regioselectivity of the arylation reaction were investigated. To a reaction where peptide 1j and 1a were mixed together both at 1 mM concentration, excess amount of perfluoroarene-containing peptide 4 was added in phosphate buffer, pH 8.0 at 37° C. LC-MS analysis of the crude reaction mixture at 30 minutes showed almost exclusively selective and quantitative arylation of the cysteine inside the π-clamp (FIG. 4, bottom chromatrogram).

Example 4

Cysteine Arylation in Complex Proteins

A large and complex protein molecule was tested: a 55 kDa model protein 6 that had a free N-terminal cysteine and C-terminal Phe-Phe π-clamp. In order to confirm the regioselectivity of the labeling reaction, a protease cleavage site was engineered next to the π-clamp sequence. Thus the regioselectivity can be unequivocally determined by digestion of the labeled product with tobacco itch virus (TEV) protease. Upon reacting protein 6 with perfluoroaryl-modified peptide 4 for 2 hours, almost quantitative formation of the mono-labeled product 7 was observed, and the N-terminal free cysteine could be further labeled with fluorescein-5-maleimide producing only the dual-labeled product 9. Subjecting protein 9 to TEV cleavage led to exclusive generation of protein 10, which confirmed the absolute regioselectivity of the π-clamp-directed cysteine arylation reaction. So, the π-clamp-directed cysteine arylation expands the scope of previous cysteine modification methods, which necessitate the use of protecting group, multiple steps, or special protein structures to differentially functionalize two or multiple cysteines.

Example 5

Cysteine Arylation of Proteins with Multiple Essential Cysteines

Figure 6:
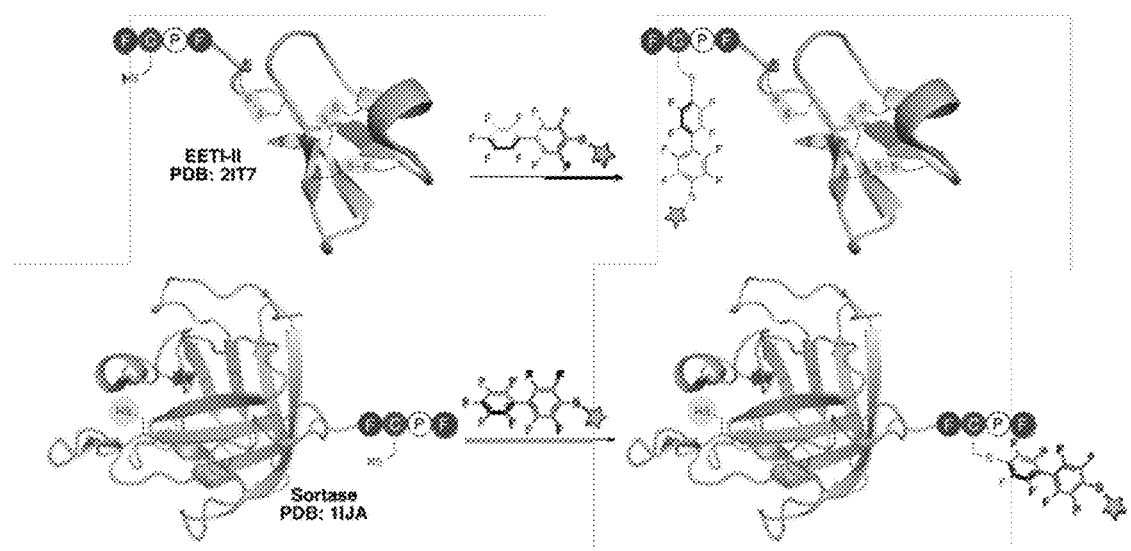
FIG. 6 depicts schematically single-site-specific labeling of cysteine/disulfide rich proteins by π-clamp-directed cysteine arylation (peptides disclosed as SEQ ID NOS 5, 5, 5 and 5, respectively, in order of appearance).

The π-clamp-directed arylation chemistry will be applied to modification of proteins with multiple essential cysteines and/or disulfides. These proteins cannot be modified by conventional cysteine modification approaches. Two model proteins have been chosen: EETI-II (ecballium elaterium trypsin inhibitor II) and sortase (FIG. 6). EETI-II is a 28-amino acid small protein of the knottin family; it contains three disulfide bonds and forms a rigid scaffold with multiple solvent-exposed loops, which have been previously engineered to generate various peptide-based binders. Sortase is a widely used transpeptidase that contains an essential cysteine that is responsible for its enzymatic activity. Extending the application of cysteine modification toolkit to these cysteine/disulfide rich proteins will expand the pool of cysteine tagging techniques. This technique may be useful in the production of homogenous antibody-drug conjugates for which highly site-specific protein conjugation techniques are desired.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

---

We claim:

1. A method according to Scheme 1:

Scheme 1 wherein, independently for each occurrence,
  base is a Bronsted base;
  $A^1$ is H, an amine protecting group, a natural or unnatural alpha amino acid, a peptide, an oligopeptide, a polypeptide, or a protein;
  $A^5$ is OH, —O(carboxylate protecting group), a natural or unnatural alpha amino acid, a peptide, an oligopeptide, a polypeptide, or a protein;
  x is 0, 1, 2, 3, 4, 5, or 6;
  R is H or alkyl;
  $R^2$ is aralkyl or heteroaralkyl;
  $R^3$ is aralkyl or heteroaralkyl;
  ⓑ is a perfluorinated aryl radical; and
  ⓑ¹ is a perfluorinated aryl para-substituted diradical.

2. The method of claim 1, wherein the base is triethylamine, $Na_3PO_4$, or tris(hydroxymethyl)aminomethane.

3. The method of claim 1, wherein $R^2$ is benzyl, indolylmethyl, or hydroxybenzyl.

4. The method of claim 1, wherein $R^3$ is benzyl, indolylmethyl, or hydroxybenzyl.

5. The method of claim 1, wherein R is H.

6. The method of claim 1, wherein x is 1, 2, or 3.

7. The method of claim 1, wherein ⓑ is pentafluorophenyl or 4'-(2,2',3,3',4,5,5',6,6'-nonafluoro-1,1'-biphenyl).

8. The method of claim 1, wherein ⓑ comprises at least one $^{18}F$ isotope.

9. A compound comprising substructure I or substructure II:

wherein, independently for each occurrence,
  $A^1$ is H, an amine protecting group, a natural or unnatural alpha amino acid, a peptide, an oligopeptide, a polypeptide, or a protein;
  $A^5$ is OH, —O(carboxylate protecting group), a natural or unnatural alpha amino acid, a peptide, an oligopeptide, a polypeptide, or a protein;
  ¹ is a perfluorinated aryl para-substituted diradical;
  x is 0, 1, 2, 3, 4, 5, or 6;
  R is H or alkyl;
  $R^1$ is H, alkyl, thioalkyl, alkylthioalkyl, aralkyl, heteroaralkyl, hydroxyaralkyl, $HO_2C$-alkyl, $H_2N$—C(O)-alkyl, heterocycloalkyl, guanidinylalkyl, aminoalkyl, or hydroxyalkyl;
  $R^2$ is aralkyl or heteroaralkyl; and
  $R^3$ is aralkyl or heteroaralkyl.

10. The compound of claim 9, wherein R² is benzyl, indolylmethyl, or hydroxybenzyl.

11. The compound of claim 9, wherein R³ is benzyl, or indolylmethyl, or hydroxybenzyl.

12. The compound of claim 9, wherein ¹ is 2,3,5,6-tetrafluorophenylene or 2,2',3,3',5,5',6,6'-octafluoro-1,1'-biphenyl-4,4'-ene.

13. The compound of claim 9, wherein R is H.

14. The compound of claim 9, wherein x is 1, 2, or 3.

15. The compound of claim 9, wherein the compound comprises a substructure selected from the group consisting of (peptides disclosed as SEQ ID NOS 1-2, respectively, in order of appearance):

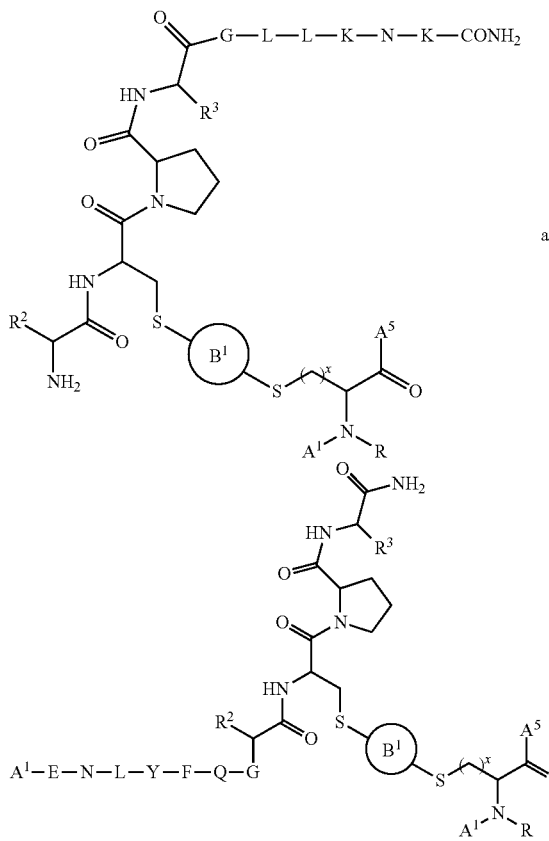

and

16. The compound of claim 9, wherein the compound comprises a substructure selected from the group consisting of (peptides disclosed as SEQ ID NOS 1-2, respectively, in order of appearance):

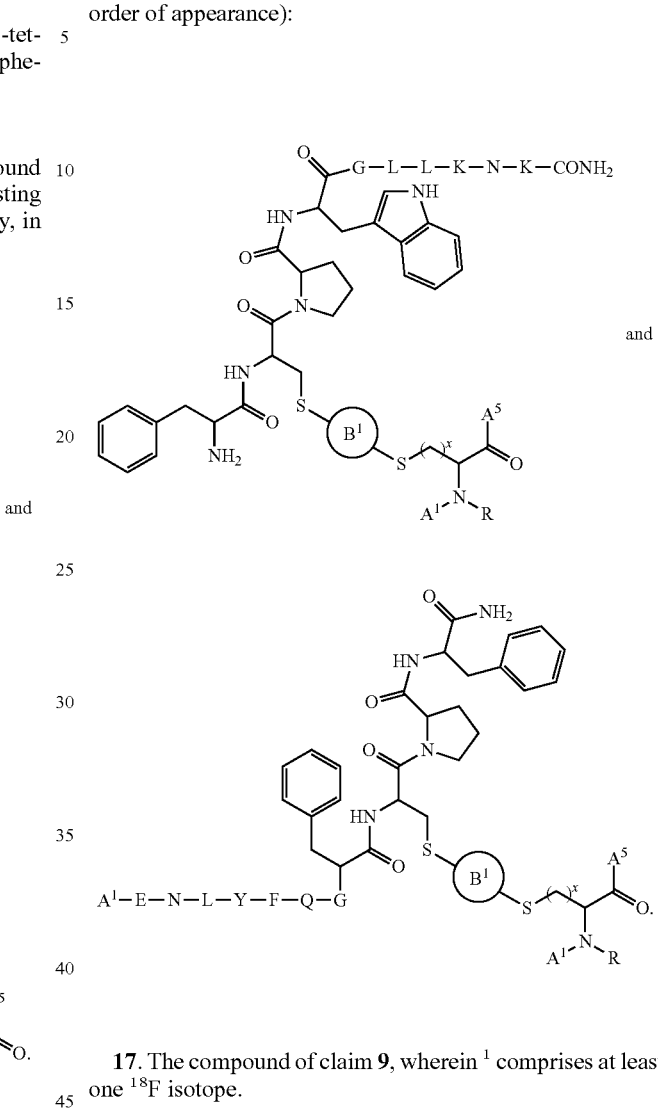

17. The compound of claim 9, wherein ¹ comprises at least one $^{18}$F isotope.

* * * * *

UNITED STATES PATENT AND TRADEMARK OFFICE
CERTIFICATE OF CORRECTION

PATENT NO. : 9,181,297 B1
APPLICATION NO. : 14/278060
DATED : November 10, 2015
INVENTOR(S) : Pentelute et al.

Page 1 of 1

It is certified that error appears in the above-identified patent and that said Letters Patent is hereby corrected as shown below:

TITLE PAGE ITEMS 71 AND 72 SHOULD READ

Bradley L. Pentelute, Cambridge, MA (US);

Chi Zhang, Cambridge, MA (US);

Peng Dai, Cambridge, MA (US)

Signed and Sealed this
Ninth Day of August, 2016

Michelle K. Lee
*Director of the United States Patent and Trademark Office*

SEQUENCE LISTING

```
<160> NUMBER OF SEQ ID NOS: 12

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Leu Leu Lys Asn Lys
1               5

<210> SEQ ID NO 2
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any natural or unnatural alpha amino acid or
      absent
<220> FEATURE:
<223> OTHER INFORMATION: See specification as filed for detailed
      description of substitutions and preferred embodiments

<400> SEQUENCE: 2

Xaa Glu Asn Leu Tyr Phe Gln Gly
1               5

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Asn Leu Tyr Phe Gln Gly Cys Lys Lys Lys
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Thr Leu Pro Ser Thr Cys Gly Ala Ser
1               5                   10

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Phe Cys Pro Phe
1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Phe Cys Pro Trp
1

<210> SEQ ID NO 7
<211> LENGTH: 10
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 7

Phe Cys Pro Trp Gly Leu Leu Lys Asn Lys
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Cys Pro Gly Gly Leu Leu Lys Asn Lys
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly, Tyr, Trp or Phe
<220> FEATURE:
<221> NAME/KEY: MOD_RES
<222> LOCATION: (4)..(4)
<223> OTHER INFORMATION: Gly, Tyr, Trp or Phe
<220> FEATURE:
<223> OTHER INFORMATION: See specification as filed for detailed
      description of substitutions and preferred embodiments

<400> SEQUENCE: 9

Xaa Cys Pro Xaa Gly Leu Leu Lys Asn Lys
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Phe Cys Pro Phe Gly Leu Leu Lys Asn Lys
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Asn Leu Tyr Phe Gln Gly Phe Cys Pro Phe
1               5                   10

<210> SEQ ID NO 12
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 12

Glu Asn Leu Tyr Phe Gln
1               5
```